US012073660B2

(12) United States Patent
Arroyo et al.

(10) Patent No.: US 12,073,660 B2
(45) Date of Patent: Aug. 27, 2024

(54) SYSTEM AND METHOD FOR MONITORING THE STATE OF THE OIL OF TRUCK WHEELS

(71) Applicant: KOMATSU REMAN CENTER CHILE S.A., Santiago (CL)

(72) Inventors: Gonzalo Arroyo, Santiago (CL); Álvaro Orellana, Viña del Mar (CL)

(73) Assignee: KOMATSU REMAN CENTER CHILE S.A., Santiago (CL)

( * ) Notice: Subject to any disclaimer, the term of this patent is extended or adjusted under 35 U.S.C. 154(b) by 505 days.

(21) Appl. No.: 17/601,364

(22) PCT Filed: May 7, 2019

(86) PCT No.: PCT/CL2019/050035
§ 371 (c)(1),
(2) Date: Oct. 4, 2021

(87) PCT Pub. No.: WO2020/198894
PCT Pub. Date: Oct. 8, 2020

(65) Prior Publication Data
US 2022/0180672 A1 Jun. 9, 2022

(30) Foreign Application Priority Data
Apr. 5, 2019 (CL) .................... 0931-2019

(51) Int. Cl.
*G07C 5/00* (2006.01)
*B60B 19/08* (2006.01)
(Continued)

(52) U.S. Cl.
CPC ............ *G07C 5/008* (2013.01); *F16N 29/02* (2013.01); *F16N 29/04* (2013.01); *G07C 5/006* (2013.01); *G07C 5/0808* (2013.01); *B60B 19/08* (2013.01)

(58) Field of Classification Search
CPC ...... G07C 5/008; G07C 5/006; G07C 5/0808; F16N 29/02; F16N 29/04; F16N 2200/00;
(Continued)

(56) References Cited

U.S. PATENT DOCUMENTS

| 4,782,332 A | 11/1988 | Cipris et al. |
| 5,789,665 A | 8/1998 | Voelker et al. |
| 2009/0201036 A1 | 8/2009 | Hedges et al. |
| 2017/0087990 A1 | 3/2017 | Neti et al. |

FOREIGN PATENT DOCUMENTS

| AU | 2015249207 A1 | 11/2015 |
| CN | 204943003 U | 1/2016 |

(Continued)

OTHER PUBLICATIONS

International Search Report and Written Opinion mailed Jan. 3, 2020, directed to International Application No. PCT CL2019/050035; 20 pages.

*Primary Examiner* — Peter J Macchiarolo
*Assistant Examiner* — Anthony W Megna Fuentes
(74) *Attorney, Agent, or Firm* — Morrison & Foerster LLP

(57) ABSTRACT

System and method for constantly monitoring the state of the oil of the wheels of heavy machinery, in particular mining trucks, while they are in motion. Comprising a server; a wireless sensor module attached to the rim of the wheel, obtaining oil measurements from an oil quality sensor, which sends the measurements to the server wirelessly; the sensor, located inside the sensor module; and a spoon-type mechanism which maintains the sensor in permanent contact with the oil inside the wheel, wherein said spoon-type mechanism rotates with the sensor module and the wheel. In addition, it may comprise a receiving antenna module which is located between the sensor module and the server. In addition, it may comprise a transmitter which is (Continued)

located between the receiving antenna module and the server.

17 Claims, 8 Drawing Sheets

(51) Int. Cl.
    *F16N 29/02*     (2006.01)
    *F16N 29/04*     (2006.01)
    *G01N 33/28*     (2006.01)
    *G07C 5/08*     (2006.01)
    *B60C 17/10*     (2006.01)
    *G08C 17/00*     (2006.01)
    *G08C 25/00*     (2006.01)

(58) Field of Classification Search
    CPC ............ F16N 2210/04; F16N 2210/12; F16N 2230/02; B60B 19/08; B60B 2900/561; B60Y 2200/41; B60C 17/10; G01N 33/28; G08C 17/00; G08C 25/00
    See application file for complete search history.

(56) References Cited

FOREIGN PATENT DOCUMENTS

| | | | | |
|---|---|---|---|---|
| CN | 109073506 A | * | 12/2018 | ............... G01K 7/02 |
| CN | 109073506 A | | 12/2018 | |
| WO | 2019/060728 A1 | | 3/2019 | |

* cited by examiner

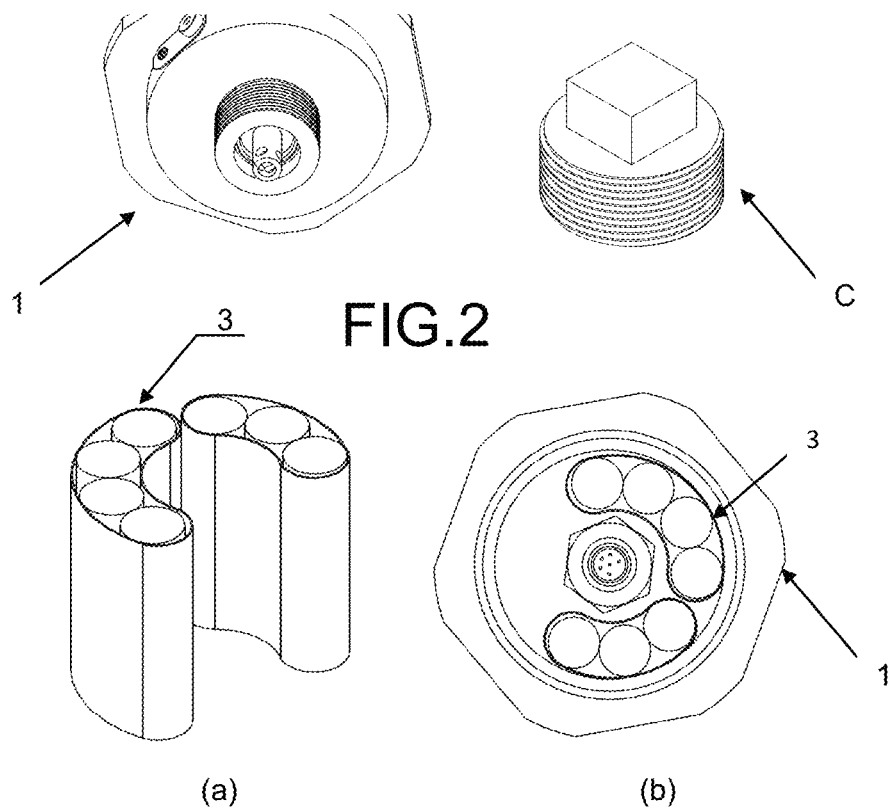
FIG.2
FIG.3
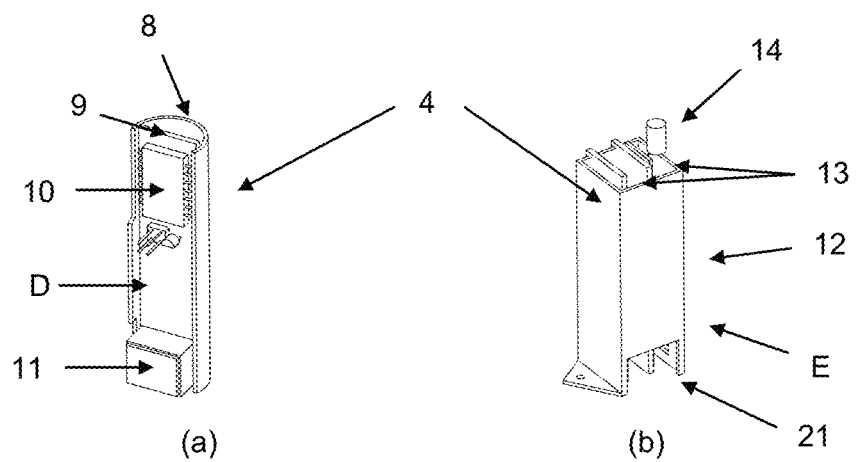
FIG.4

SYSTEM AND METHOD FOR MONITORING THE STATE OF THE OIL OF TRUCK WHEELS

CROSS-REFERENCE TO RELATED APPLICATION

This application is a U.S. national stage patent application of International Patent Application No. PCT/CL2019/050035, filed on May 7, 2019, which claims priority of CL931-2019, filed on Apr. 5, 2019, the entire contents of each of which are incorporated herein by reference.

FIELD OF THE DISCLOSURE

The invention relates to the constant monitoring of the state of the oil of the wheels of heavy machinery, such as the wheels of mining trucks, especially electric trucks, wherein the wheel is an electric engine coupled to a mechanical engine with planetary gearbox for the transmission of torque, wherein each planetary gearbox has lubricating oil that is rotating inside the wheel. Monitoring is done in order to detect, early and automatically, defects in the mechanical part of the engine, through changes in the lubricating oil, wherein said monitoring is done through a system that includes an autonomous sensor that rotates with the truck wheel in movement, using the different variables that the sensor emits in order to detect anomalies in the transmission oil and to thereby determine defects in the mechanical engines of mining trucks.

BACKGROUND OF THE DISCLOSURE

The system and method of the present invention continuously and remotely monitors the appearance of defects in the mechanical part of the electric engine through changes in the oil inside the wheels of mining trucks. Said changes are measured through a sensor that has direct access to the oil contained in the engine, wherein the data issued by the sensor is analyzed automatically in order to arrive at a judgment regarding the type of defect occurring in the truck. In one embodiment, analysis of the data issued by the sensor in contact with the oil is supplemented by analysis of the electric signature of the electric engine that is coupled to the mechanical part so as to improve the performance and efficiency of the detection of defects.

Detected changes in the oil may be of different types: contamination (water, dust, another oil—for example, brake oil), particulate material due to waste, changed viscosity, excessive heat, etc.

The electric signature is the characteristic pattern of the electric current of a rotating machine and it can reflect the condition, not only of the electric machine, but also, in addition, of connected systems, both mechanical and electrically to the rotating machine, such as the engine, generator, which work with alternating current (AC) or direct current (DC), such as those of mechanical transmission, the rectifier system and the inverter system, among others. It has succeeded in identifying the electric signature of a set of defects or anomalies which are commonly found in electric engines and alternators. With which the signature data can be used indirectly to analyze the existence of changes in the oil inside the wheels. This is how the oil data obtained by the sensor of the invention will be able to communicate an anomaly in the usual oil settings, demonstrating a probable defect in the mechanical part of the engine. The analysis of the electric will reveal possible defects in the electric and/or mechanical portion, in particular in the mechanical part coupled to the electric engine. Therefore, with the information from these two different systems, acting together (sensor data and electrical signature data), the appearance of defects in the truck can be detected with greater certainty.

Document CN204943003 (U) refers to a mining truck and a means of checking from an oil lubrication station. The means of checking of this oil lubrication station is equipped with a monitoring component, a joining component and a fixed component. The monitoring component includes the startup and locking of the lubrication check of the lubricant from the oil lubrication station, of the connection of the checking component with the oil lubrication station. The fixed component with the oil lubrication station checking means is arranged in the oil lubrication station. The checking means of this oil lubrication station, are used to check the operational status of the oil lubrication station. Using the above-described design, it is possible to focus the adjustment on the oil lubrication station with lubrication check, the operational condition of the lubricant pump, when it is appropriate for the direct visual inspection to improve maintenance efficiency, ensure the reliable and stable work yield of the oil lubrication station.

Document U.S. Pat. No. 5,789,665 (A) refers to a method and device to determine the deterioration of lubrication oil measuring the electrical properties of a polymeric matrix (support) that contains charged ionic groups. The dynamic range of the device increases, creating a local polar environment around the charged groups of the polymeric matrix and exploding the contraction of a cord with an increasing deterioration (or solvent polarity). Both focal points can be used in addition in the single sensor by means of the use of multiple chambers that contain a combination of the above. In addition, the detection of contaminants improves through checking changes in the amplitude and/or frequency of the exiting noise. The sensor can also be used to detect an oil level, for example, in an engine oil housing.

Document U.S. Pat. No. 4,782,332 (A) refers to a sensor improved by in situ use in an electrical circuit which sensor is corroded as a result of the deterioration of the oil and provides a changing electrical current due to the increased resistance of said corrosion. Preferentially, the sensor is a ceramic tube that has a first layer of nickel deposited without current onto it, with a second layer of electrolytic lead. The cables join at the ends of the tube and the sensor can be used in situ in oil in order to measure the deterioration of the quality of the oil as a result of its corrosion and of changes in resistivity.

Document US2009201036 refers to a detection component that comprises a non-conductive housing with three chambers to detect the conductivity of the oil, the depletion and oxidation of the additive, and the contamination of the water, respectively. By monitoring a series of oil sensors, an early detection of the deterioration of the oil, due to oxidation, is provided. The monitoring system also detects the excess of soot, water and other contaminants in the oil. The set of oil sensors and the related monitoring system decrease the probability of catastrophic failure of the engine by early detection and warning of a decrease in the quality of the oil, costs for the owners of vehicles for service and elimination fees while they help to meet environment protection standards.

In these documents, the use of checking means or sensors for measuring the condition of the lubrication oil is disclosed. In all these cases, the means of checking and/or the sensors are static and not in movement, such that the possibility of taking measurements in movement is nonexistent due to the configuration of said sensors and/or checking means, since these deteriorate and would not meet their objective of measuring the variables in question.

Document US2017087990 (A1) refers to a system and method for predicting a mechanical failure. A system and method for monitoring a motor vehicle that monitors the operating conditions for the vehicle system and determines if the operating conditions of the vehicle system meet the designated operating conditions. In response to determining that the operating conditions of the vehicle system that are being monitored meet the designated operating conditions, an electrical signature representative of an electrical current supplied to the engine of the vehicle system is examined and it is determined if one or more of the vehicle engines are damaged, the mechanical system or coupling of the engine or one or more wheels or axles of the vehicle system is identified based on the electrical signature in question.

Document AU2015249207 (A1) refers to a system and method for predicting mechanical failures of an engine. The method includes the monitoring of the primary characteristics of an electrical signal supplied to a traction engine of a vehicle during a first detection window. The primary characteristics represent a first electrical signature of the traction engine and are checked as measurements of the electrical current supplied to the traction engine before the electrical current arrives at the traction engine. The method also includes deriving one or more signature values from a first mathematical model of the first electrical signature of the engine, predicting a mechanical failure of the traction engine based on one or more signature values, and automatically generating a vehicle checking signal to change one or more from a traction force or braking force of the vehicle in response to the prediction of a mechanical failure.

In these last two documents, the use of an electrical signature for determining defects in truck engines, or in vehicles in general, is disclosed. Nonetheless, there is no relation to the measurement of the lubricating oil settings.

SUMMARY OF THE DISCLOSURE

According to some embodiments, this invention monitors, continuously and remotely, the appearance of defects in the mechanical portion of the electrical engine through changes in the oil inside the back wheels of mining trucks, on the basis of the settings of the oil contained in said wheels, via a system for monitoring the state of the oil in the wheel, wherein said wheel is an electrical engine coupled to a mechanical engine with a planetary mechanism for the transmission of torque, continuously evaluating the condition of the oil lubrication of the transmission system, using a sensor that with the use of a self-leveling or spoon-type mechanism, maintains said sensor in constant contact with the oil. In addition, in one of the embodiments, the analysis of the different variables issued by the sensor that is in constant contact with the oil in order to detect anomalies in the transmission oil, is supplemented with the analysis of the electrical signature and thereby succeeds in detecting defects in mechanical engines of mining trucks.

BRIEF DESCRIPTION OF THE FIGURES

The disclosure will now be described, by way of example only, with reference to the accompanying drawings, in which:

FIG. 2 shows details of the coupling par of the wireless sensor module and plug or magnetic buffer used in wheels that is replaced by the wireless sensor module;

FIG. 3 shows details of the energy source as a battery pack (a) for a wireless sensor module and a distribution means (b) on the coupling part, in concentric form;

FIG. 4 show details of the electronic module of the wireless sensor module, that consists of a feed module (a) and a checking module (b);

DETAILED DESCRIPTION OF THE DISCLOSURE

According to some embodiments, the system of the invention includes a wireless sensor module that comprises an autonomous sensor, that rotates with the truck wheel the objective of which is to continuously the condition the condition of the oil lubrication of the transmission system. The sensor has a mechanical device for which a system of self-leveling or spoon-type device has been designed that maintains the nose of the sensor in contact with the oil.

The wireless sensor module is, preferably, integrated into the rear wheel, replacing a magnetic buffer for said wireless sensor module (it can also be applied in any other place in the wheel that makes contact with the oil possible or the wireless sensor module can also be located in the front wheels where there is no engine, but there is oil. The wheel and the wireless sensor module rotate while the truck moves forward, or remains stationary. The system of the invention is energy-autonomous and wireless, using an energy source, in addition has a sensor that measures various settings such as: amount of particulate material, temperature, contamination (such as water, dust, a different type of oil), permittivity, viscosity, etc. (there are two different sensors in the invention, one in each rear wheel, but the principle can be applied to any sensor and any variable of oil that can be measured).

The energy source can be a rechargeable battery or not, or can be energy storing batteries coupled to sources of solar energy, or sources of energy generated by vibrations/movement, wherein a device transforms the vibrations/movements of the wheel into current and voltage, or sources of energy generated by differences in temperature, wherein a device transforms the energy generated by temperature differences into current and voltage. Wherein the temperature difference is measured by the Peletier thermo-electric effect, between the temperature of the oil that is in contact with the sensor nose and the outside air temperature in contact with a wall of the sensor.

Figure 10:
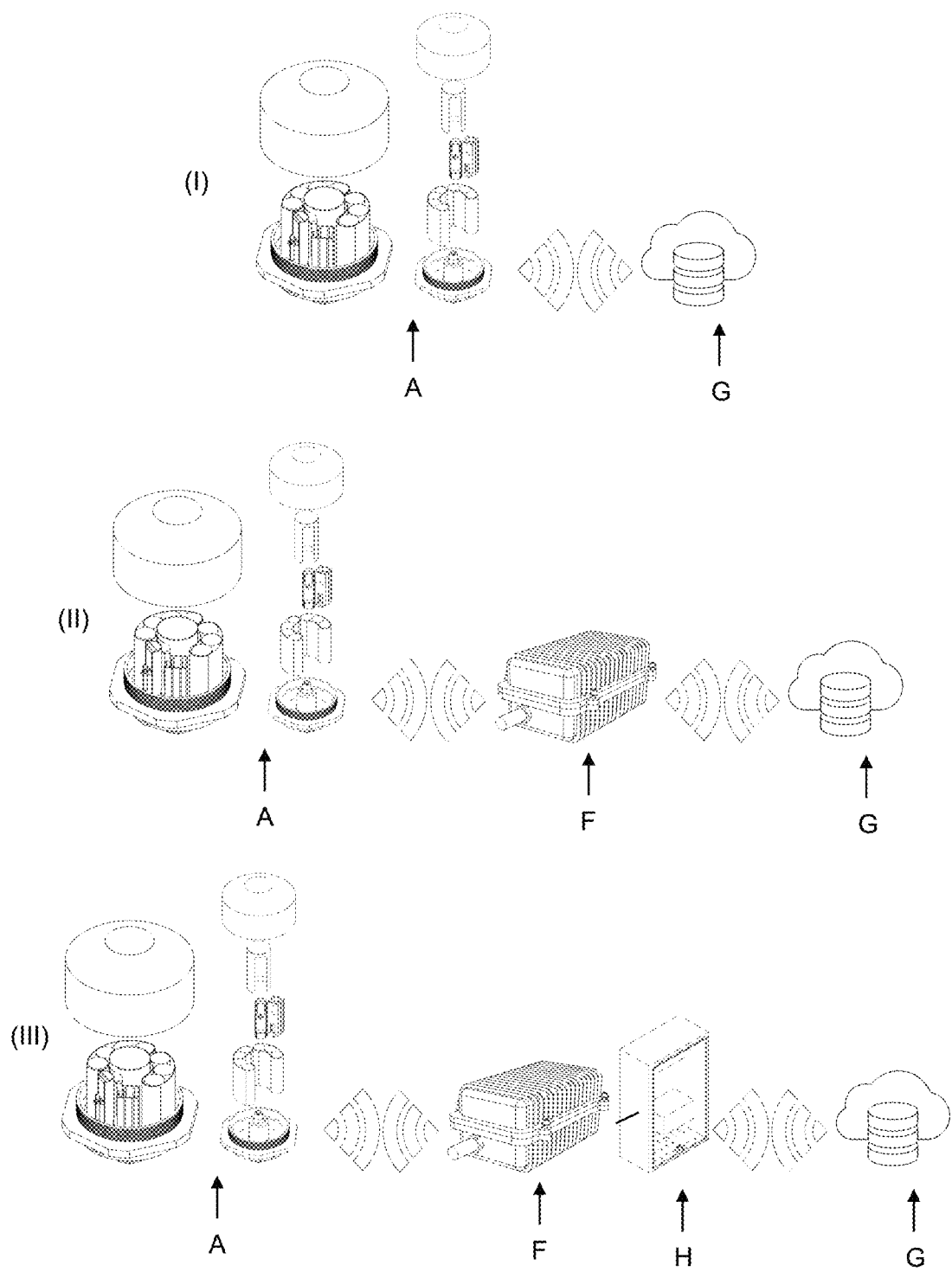
FIG. 10 shows communication embodiments I, II and III, between the wireless sensor module and the server.

The wireless sensor module (A) can communicate with a data server (G) basis for checking the system in three embodiments (embodiments I, II and III, see FIG. 10):

I: The wireless sensor module (A) wirelessly sends all of the data collected by the sensor (5) directly to a data server (G), wherein the means of communication between the wireless sensor module (A) and the server (G) is via radio-frequency (RF) technology, using different protocols enabling connection to the Internet (GSM, UMTS, HSPA, LTE, Wi-Fi and others that may appear in the future).

II: The wireless sensor module (A) sends the data collected by the sensor (5) to a receiving antenna (F) at the side of the truck, wirelessly, which in turn wirelessly sends the data to the server (G), wherein the means of communication between the wireless sensor module (A) and the antenna (F) is RF type and wherein the protocols that can be used between the wireless sensor module (A) and the antenna (F) are Bluetooth-type protocols such as GSM, UMTS, HSPA, LTE, Wi-Fi, Zigbee and others that may appear in the future, and wherein communications between the antenna (F) and the server (G) are RF type, using protocols that make an Internet connection possible (GSM, UMTS, HSPA, LTE, Wi-Fi and others that may appear in the future).

III: The wireless sensor module (A) wirelessly sends the data collected by the sensor (5) to a receiving antenna (F) at the side of the truck, where the receiving antenna (F) is wirelessly connected to a box with processing capacity and transmission or transmitter (H), wherein this processing box or transmitter (H) compiles the data and uploads it to the server (G) so that any user with access to the server (G) may get the sensor measurements (5) via the Internet. Wherein the means of communication between the wireless sensor module (A) and the antenna (F) is RF type and wherein the protocols that can be used between the wireless sensor module (A) and the antenna (F) are Bluetooth-type protocols such as GSM, UMTS, HSPA, LTE, Wi-Fi, Zigbee and others that may appear in the future, and wherein communications between the antenna (F) and the server are RF type, using protocols that make an Internet connection possible (GSM, UMTS, HSPA, LTE, Wi-Fi and others that may appear in the future).

With the server (G) data, the user will have the ability to make decisions regarding the settings measured within the lubrication oil and alarms generated automatically by the system.

Since the sensor (5) must be in permanent contact with the oil in order to get a reliable reading, the system includes a spoon-type mechanism (7) or self-leveling device coupled to the sensor (5), wherein the spoon-type mechanism (7) or self-leveling device corresponds to a mechanical device that collects the oil and maintains it in permanent contact with the nose of the sensor (5) wherein the measuring is conducted. The device or spoon-type mechanism (7) rotates with the wheel (B) and keeps the oil horizontal in order to avoid a drop; there is also the option of making perforations in the spoon-type mechanism (7) in order to allow oil circulation in same.

The system of the invention must comply with the following requirements in order to be able to complete the measurements of the condition of the lubrication oil:

It must be a robust system for the conditions that it will confront in a mining site.

The sensor must be of a size and weight that can be handled by any user and must have ease of access to any change of energy source, without there being a need to remove the sensor from the wheel.

The sensor energy source must have sufficient energy autonomy for the functioning of the sensor.

The system must be able to communicate without the loss of information and without interfering with other radio-frequency equipment.

The unit where the sensor is located must be hermetically sealed and make it possible for the spoon-type mechanism to deliver oil to the nose of the system at all times.

In addition, acquire a monitoring method from the system, wherein the obtained data is processed by the monitoring system and is compared, among other options, with the electric signature.

In the case of identification of the electric signature for a set of defects or anomalies in various subcomponents of the mining truck rotating machines, which will be used to compare the data obtained by the system of the invention. These anomalies or defects are well-defined characteristics of the changes in mechanical and electrical defects of the rotating machines and systems annexed to the mining truck. The identified electrical signatures may correspond to defects or anomalies in gear teeth, bearings, mechanical unbalance, electrical unbalance, breaks in induction engine bars, condition of lubrication in the transmission system, among others. All of these details can be detected remotely by comparing the electrical signature measured on line with the electrical signature in the signatures database associated with defects in the mining truck sub-components. Transform pairs are used to improve the detection of anomalies. The most commonly used transform pair for the extraction of characteristics from the current signal is the Fourier Transform Pair or FFT. The FFT makes it possible to read the spectrum of frequencies of the current and therefore the anomalies detected by the sensor such as the presence of particulate material, overheating of the oil, deterioration of viscosity, or contamination by external agents, such as dust, water or another oil.

The settings received by the monitoring system will be analyzed and the condition of the operating engine will be evaluated as a function of the combination of variables and the history of the components that has been previously recorded. In addition, the electrical signature of the transmitted data may be used by the sensor and be analyzed, in order to determine the type of problem that is arising. The evaluation is done automatically and in real time.

Specifically, the monitoring system of the invention comprises the following components:

A Server (G) to which a user has access and where the databases with the measurement settings are stored.

A Wireless Sensor Module (A), is the device to the rim of the wheel (B) of the truck (preferably, the rear wheels). It is configured according to user requirements and obtains the oil measurements from the oil quality sensor (5) (which is found inside it). It is energy-autonomous, and when measurements are taken, it sends them wirelessly to the server (G). This device has an energy source (3), which enables autonomy and wireless operation.

A Sensor of the condition or quality of lubrication oil (5), is tasked with making the quality measurements of the oil within the wheel (B), and is located inside the wireless sensor module (A).

A mechanical Device, spoon-type (7), that maintains the oil quality sensor (5) in permanent contact with the oil in the wheel, wherein said spoon-type mechanism (7) rotates with the wireless sensor module (A) and the wheel (B).

In addition, the monitoring system of the invention may comprise:

A receiving antenna module (F) wherein the transmission of data can be done with radio frequency (RF) or via Bluetooth or via Wi-Fi, the antenna module (F) being located on the side of the truck, which wirelessly receives the lubricating oil measurement data from the wireless sensor module (A) and sends it wirelessly to the server (G).

The monitoring system of the invention may also comprise:

A processing and transmission Box or transmitter (H), capable of receiving electrical measurement signals coming from various sensors in the truck. It also receives oil measurement data, processes it, stores it in a storage medium, such as an archive, database, RAM memory or any other media that fulfills the function of storing data, backs it up and uploads it to the server (G) wirelessly. The receiving antenna module (F) is connected wirelessly to the transmitter (H), which makes communication between the wireless sensor module (A) and the transmitter (H) possible.

The wireless sensor module (A) comprises, mainly in its interior, an energy source (3), an electronic module (4) and an oil sensor (5) which must remain in constant contact with the oil inside the wheel (B).

Figure 1:
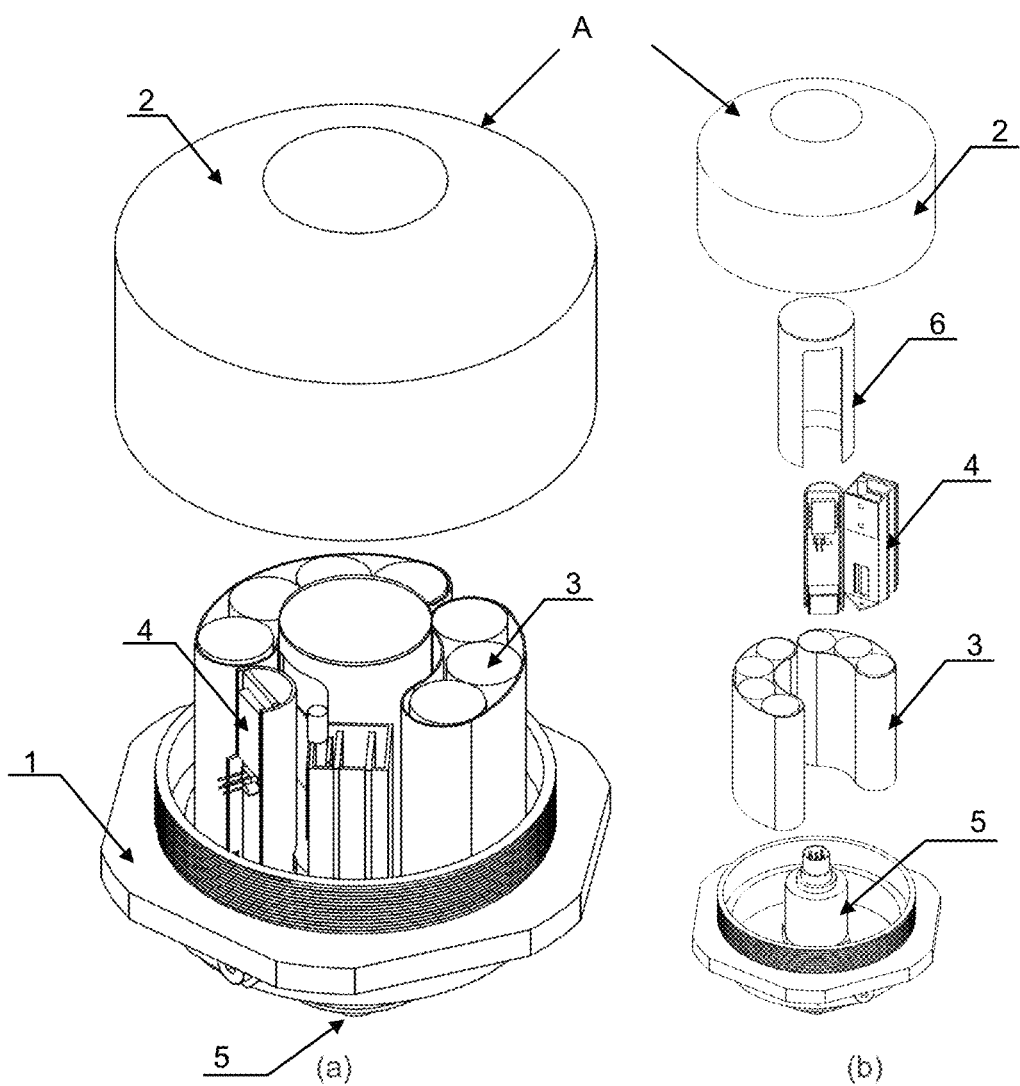
FIG. 1 shows a compact, wireless sensor module (a) and the details (b) of its components.

In FIG. 1, the preferred means of embodiment of the Wireless Sensor Module (A) with concentric distribution can be seen, with each one of its components:

Coupling piece (1): metallic piece that makes it possible to couple the module to the rim of the wheel (see details in FIG. 2). The Energy Source (3), the Electronic Module (4) and the Oil Quality Sensor (5) are concentrated in the coupling piece (1). This also makes access to the sensor on-switch (11) (seen in FIG. 4 (a)).

Dome (2): highly robust plastic piece that is tasked with protecting and hermetically sealing the components listed below.

Energy source (3) (see details in FIG. 3): tasked with delivering the energy necessary for the autonomous operation of the electronic module (4) and of the oil quality sensor (5).

Electronic module (4) (see details in FIG. 4): is comprised of two electronic capsules that execute all of the communications functions between the oil quality sensor (5) and the server (G) (communication means I) or between the oil quality sensor (5) and the receiving antenna module (F) and later to the server (G) (communication means II) or between the oil quality sensor (5) and the receiving antenna module (F) and later to the transmitter (H) and finally to the server (G) (communication means III).

Oil quality sensor (5): device that executes the measurements required by the user, within the wheel.

Central axle (6): mechanical piece that completes the function of aligning the components of the concentric embodiment around the sensor (5), inside the coupling piece (1). It also protects the oil quality sensor cable (5).

Figure 5A:
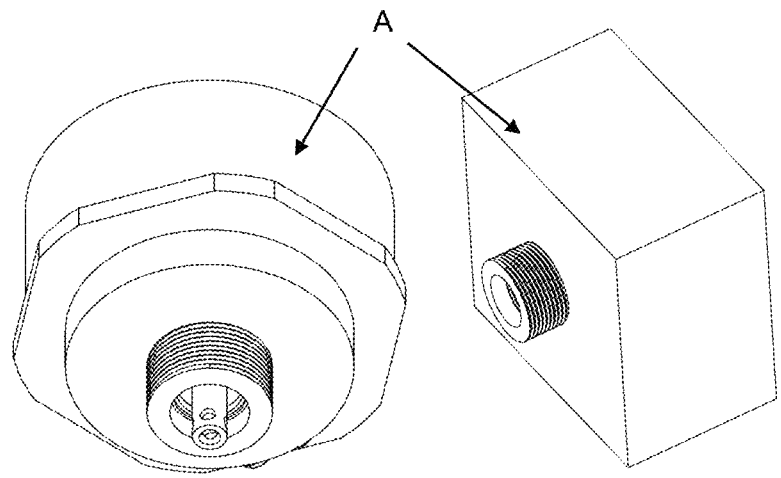
FIG. 5 shows details of two embodiments of the shape of the wireless sensor module, closed (a) and with the distribution (b) of the components inside the wireless sensor module.
Figure 5B:
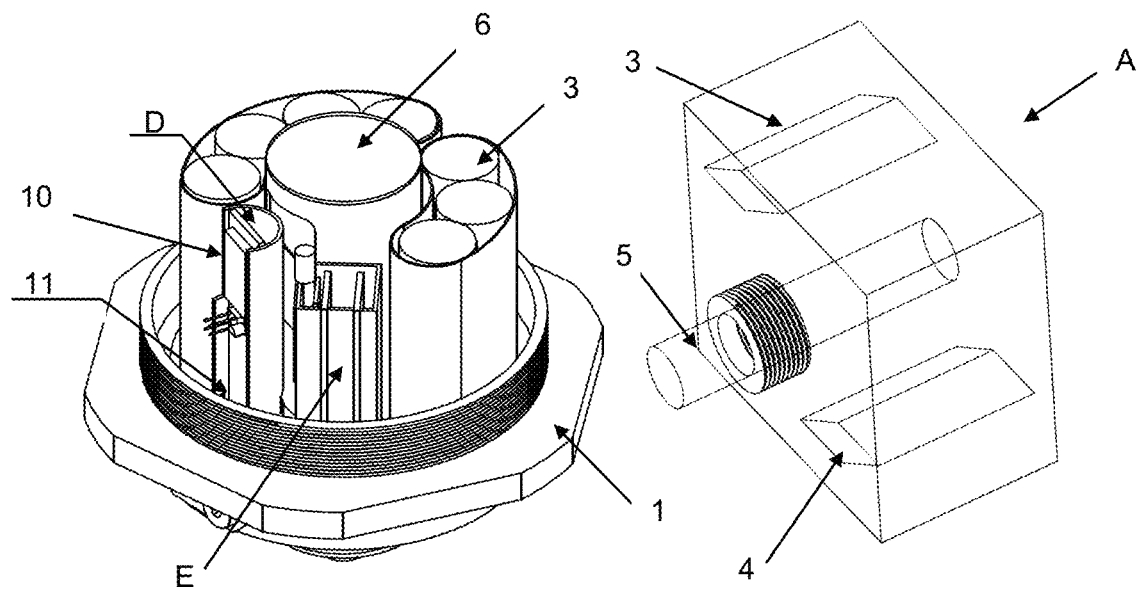

In one of the preferred embodiments, the arrangement of the internal components of the wireless sensor module (A) is done concentrically and in modules (see FIG. 5(a)). This concentric layout makes it possible to take maximum advantage of the geometry of the wireless sensor module (A) and the modularity makes it possible to handle each one of the components inside the wireless sensor module (A) independently. Nonetheless, there are various forms for laying out the principal components of the wireless sensor module (A), namely, of the energy source (3), the electronic module (4) and the oil quality sensor (5), as can be seen in FIG. 5 (b), serving the same function of protecting the components of the wireless sensor module (A) and the availability of the oil quality sensor (5) for its permanent contact with the oil inside the truck wheel.

The dome (2) of the sensor module may be designed and manufactured in UHMW (ultra high molecular weight) plastic, or in Ertacetal®, a technical plastic with better hardness and mechanical resistance properties than UHMW, wherein resistance is sought so that the thread for screwing on the housing (1) will be more resistant to wear due to use.

In FIG. 2, the detail of the coupling piece (1) of one of the embodiments of the wireless sensor module (A) can be seen, with said piece able to be made of mechanized stainless steel 316, which has excellent mechanical and resistance properties. Assembling the coupling piece (1) to the wheel is done by means of a threaded piece which emulates the top or magnetic plug (C) for the original oil, a piece replaced by the wireless sensor module (A) of the invention. For a cube-type embodiment of the wireless sensor module (A) (FIGS. 5(a) and 5(b)), the wireless sensor module (A) also has a threaded piece that emulates the original oil top (C) for the wireless sensor module (A).

Details (a) of the energy source (3) can be seen in FIG. 3, which, in this case, corresponds to a battery pack (3) and its arrangement (b) on the coupling piece (1) of the wireless sensor module (A). In this embodiment, it can be seen that the batteries in the coupling piece (1) are in a concentric layout; in addition, the packaging of the batteries is module, namely, two packets of 3 or 4 batteries (3), wherein each packet has its own connection cable. And the material used for the packaging is a heat-shrink PVC sleeve.

The electronic module is comprised of 2 modules, which can be seen in FIG. 4, the supply module (D) and the control module (E).

The supply module (D) is comprised of a profile of a corrugated or semi-circular section (8) where a printed circuit plate, PCB (9) is stored, which is exposed in order to have access to the principal connector (10) for the batteries (3) and the on/off switch (11).

The control module (E) has a square section tube (12) of stainless steel 304. Inside this are two PCBs (13), interconnected face against face. One of them has the RF communication module (not shown in figure), the antenna (14) of which extends over the tube so as not to cut off communication with the metal. The tube has lateral access (21) for the input of energy coming from the supply module (D) and for the input of cables coming from the connector of the oil quality sensor.

In the concentric layout embodiment, these modules (D and E) have a defined position inside the coupling piece (1) (see FIG. 5 (b)) and they are fixed by screws.

The supply module (D) has the on/off switch (11), making access to the switch (11) possible, without opening the wireless sensor module (A), by means of an access from the exterior with a perforation through which the switch (11) can be pressed, using a small tool (pencil, knob-type, etc.).

After accessing the on/off switch (11) this access must be hermetically closed, and to do so, this closing can be through a pin-type piece, mounted with an o-ring, or through a silicon stopper that has a flap for assembly and disassembly with the fingers, and which is inserted under pressure.

The following steps are followed, in order to obtain the wireless sensor module (A) in concentric modular shape:
 (a) The oil quality sensor (5) is screwed into the coupling piece (1).

(b) The central axle (6) is inserted under pressure onto the oil sensor (5).

(c) The battery packs (3), with polarized positions around the central axle (6) are inserted (the connectors must be facing the electronic module (4)) on the coupling piece (1).

(d) In the remaining space left by the battery pack (3), in the coupling piece (1), the electronic module (4) is attached which, in turn, is comprised of two components (D, E), interconnected with each other.

(e) The battery pack (3) connector is connected to the supply module (D), which has the on/off switch (11).

(f) The oil quality sensor (5) is connected to the control module (E) via a connector that is located in the interior (not shown in the figures) of the control module (E).

(g) The system is closed by screwing the dome (2) into the coupling piece (1), with the entire system protected and hermetic.

Figure 6:
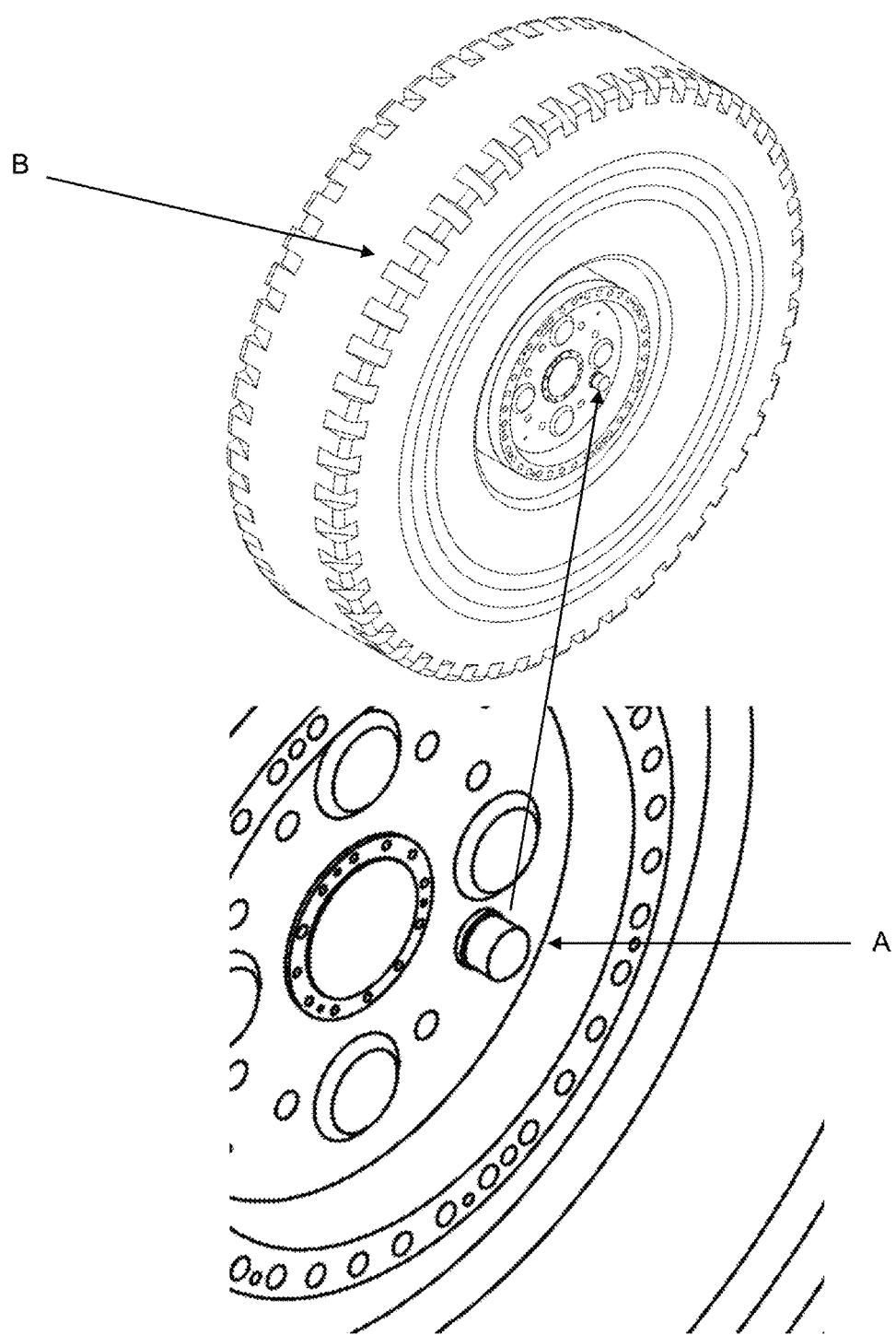
FIG. 6 shows a wireless sensor module place in the mining truck wheel.

In FIG. 6, the location of the wireless sensor module (A) can be seen, placed in the wheel (B) of the mining truck, in replacement of one of the magnetic caps in said wheel.

Figure 7A:
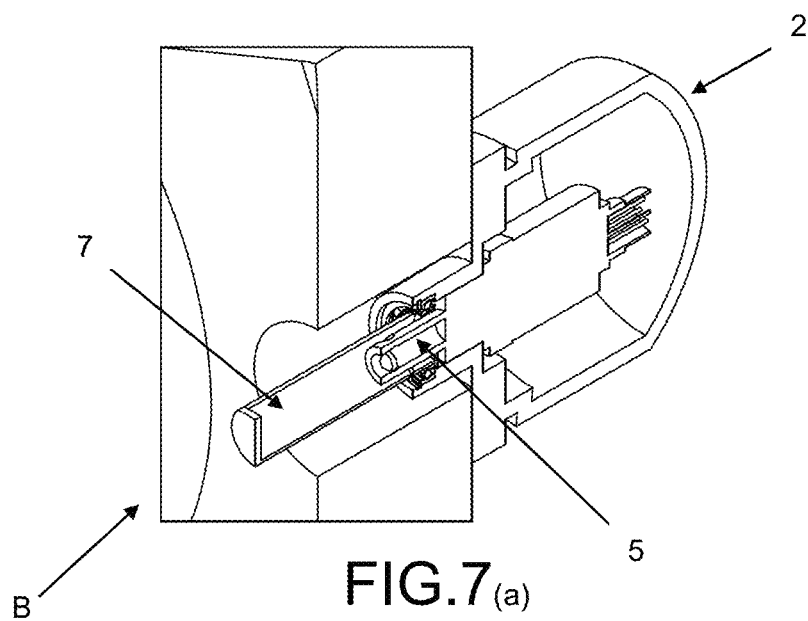
FIG. 7 shows a transverse cross section (a and b) of the wireless sensor module that shows the spoon-type mechanism that covers the oil quality sensor, inside the wheel.
Figure 7B:
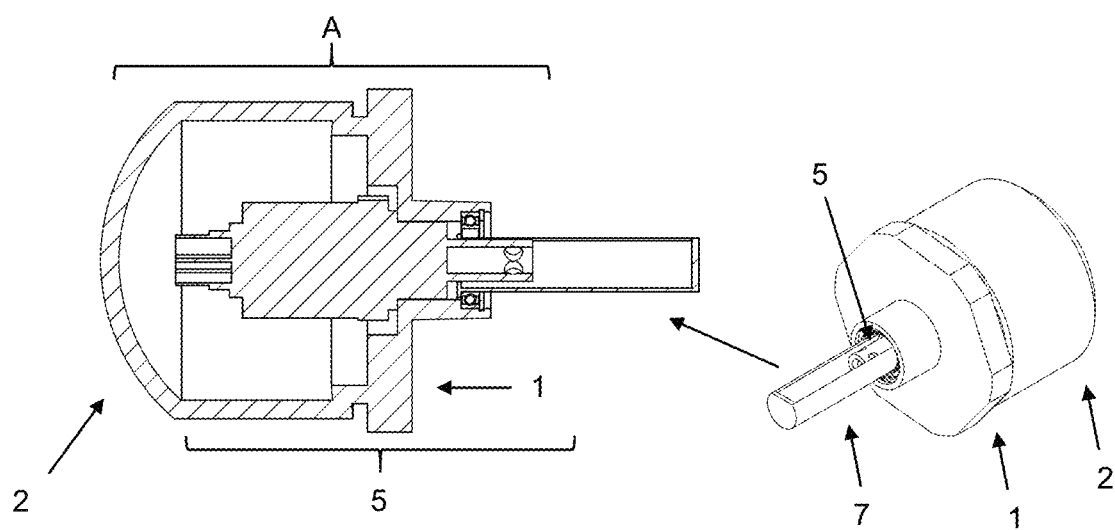

In addition to the components described above, the system comprises a mechanical device, spoon-type (7), which can be seen in FIGS. 7(*a*) and 7(*b*), wherein said spoon-type mechanism makes it possible for the oil to remain in permanent contact with the nose of the oil quality sensor (5). The spoon-type mechanism makes it possible, despite the movement of the wheel (B), for the oil to be maintained horizontal in order to avoid its dropping when the wheel rotates. In one option (not shown in the figure), the spoon-type mechanism can have several perforations so as to make it possible to regenerate or circulate oil in the spoon-type mechanism. In FIGS. 7(*a*) and 7(*b*), for greater simplicity, the quality sensor (5) inside the wireless sensor module (A) can be seen by itself.

Figure 8:
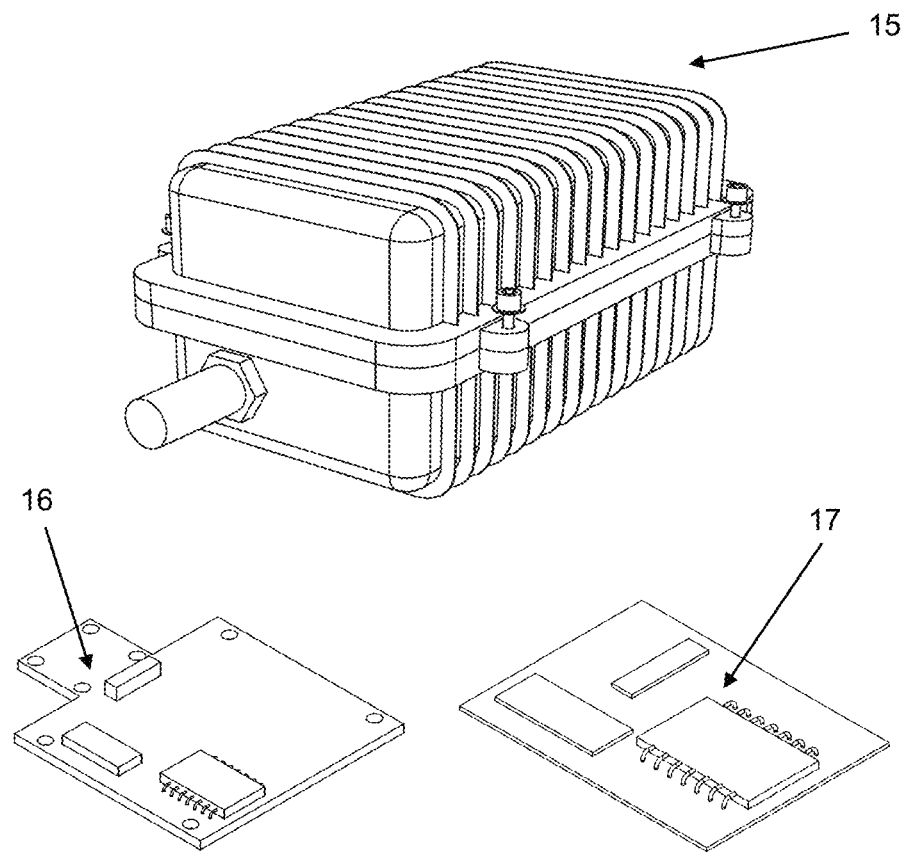
FIG. 8 shows components of the receiving antenna.

The receiving antenna module (F), located on the exterior of the mining truck, where there is an unobstructed line of sight to the wheel wherein the wireless sensor module (A) is located, is comprised by the following components, represented in FIG. 8:

A housing (15): this is a robust and water-resistant industrial level cabinet which is tasked with protecting the electronics (16) of the receiving antenna module (F), in the face of hostile environmental conditions.

An electronic module (16): is the circuit tasked with intercommunicating with the wireless sensor module (A), either directly with the server (G) (in communication embodiment II) or with the transmitter (H) (in communication embodiment III) and which is capable of sending and receiving data by RF with the wireless sensor module (A) and of communicating wirelessly with the transmitter (H) or directly, wirelessly, with the server (G).

An RF module (17): this is the receiving antenna which enables communication with the wireless sensor module (A) and with the server (G) in communication embodiment II.

Figure 9:
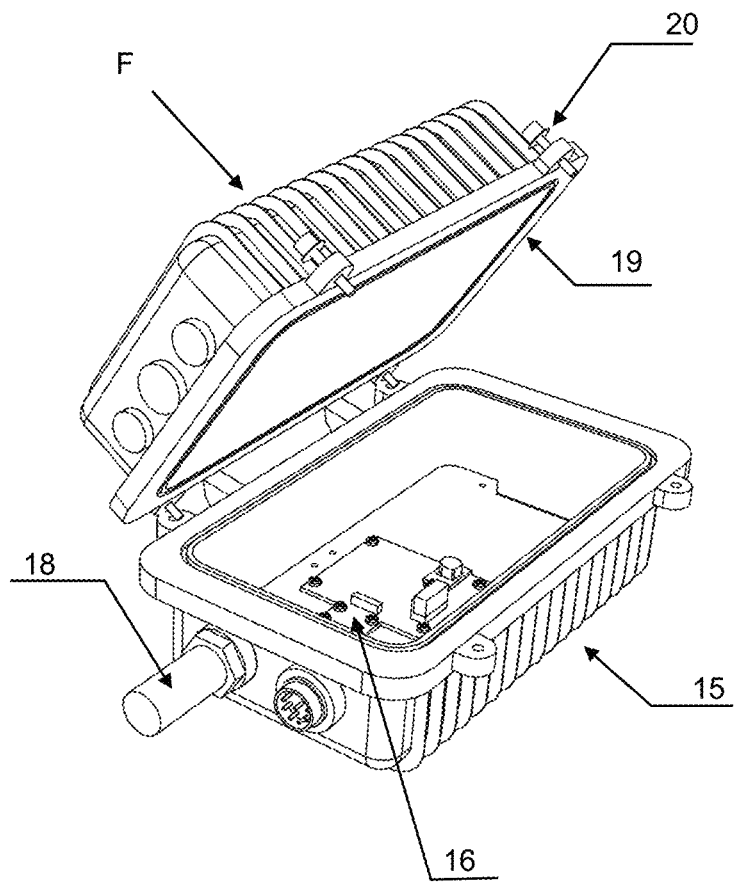
FIG. 9 shows an open housing of the receiving antenna with its components.

The components of the receiving antenna (F) can be seen in FIG. 9, which shows a diagram and photograph of the layout of each of its components.

The housing (15) of the receiving antenna module (F) is of metallic material, specifically cast aluminum, electro-painted (coating that provides it resistance to weather). The design of this housing (15) is hermetic and has an o-ring type seal around its perimeter and provides IP 66 degree of protection. The housing is closed with chased screws (20). The electronic module (16) is stored inside the housing (15), mounted by means of metallic spacers, in order to provide it with the necessary height. The RF antenna (17) is connected to this electronic, mounted on a plastic capsule-type piece (18) on the exterior of the housing (15), in order to prevent the metal from blocking the signal. The assembly of this plastic capsule (18) is done by screws, and is completely hermetic, in order to provide protection to both the RF antenna (17) and to the interior of the housing. The connection of the RF antenna module is done through a plastic-burlap medium (19) wherein said connector connects wirelessly to the transmitter (H).

The assembly of the RF antenna module to the side of the truck can be done with a stainless steel metallic plate 316, or with an omega-type clamp (in the case of assembly in tube, rail, etc.) or fastened with a band-type clamp of stainless steel 316. The assembly of the RF antenna module must be such that there is no interference between the line of the RF antenna (17) and the oil quality sensor (5) in the interior of the wheel (B), with which the position of the housing (15) must be such that the RF antenna (17) is pointed toward the oil quality sensor (5) which is located inside the wheel (B), either in front or on the side.

The transmitter (H) has the following components:

A CPU: Consisting of an industrial-type controller with processor, which is tasked with receiving the data from the oil quality sensor (5) which is found inside the wheel (B) of the mining truck, generating measurement archives, backing them up and uploading them to the server (G).

An energy source, which can be chosen from rechargeable batteries or not, UPS, supply from the truck, solar energy, etc.

A device that enables communication between the transmitter (H) and the server (G), such as, for example, a 3G/4G module (or whichever is available at the time), plus an antenna, thus enabling the connection of the Internet to the CPU.

In addition, optionally, the transmitter (H) has:

A GPS system: Device capable of detecting the physical location of the truck and sending it as data to the CPU.

Input portals for analog/digital signals, such as, for example, a USB Hub, which is a component capable of multiplexing a USB port from the CPU into various USB ports.

A USB/RS-422 converter: Device that is capable of sending, by USB to the CPU, the data received by RS-422 from the receiving antenna modules of the back wheels of the mining truck. The transmitter (H) has two converters, one on each receiving antenna module (F).

The method for monitoring the status of the oil in the wheels of a mining truck comprises the following steps for the principal communication embodiment (I) of the system of the invention:

(a) Providing a wireless sensor module (A) to replace a magnetic cap in at least one of the wheels (B) of the mining truck with said module;

(b) Measuring, through the wireless sensor module (A) one or more parameters in the transmission system oil of the at least one wheel (B) of the mining truck, chosen from among: amount of particulate matter, temperature, contamination, permittivity or viscosity, through an oil quality sensor (5) that is located inside the wireless sensor module (A);

(c) Providing a server (G) where the databases with the measurement settings are stored.

(d) Transmitting the measurement data of the setting(s) wirelessly to the server (G) from the wireless sensor module (A);
(e) Processing the obtained data and included in the data base and comparing it with data recorded earlier;
(f) Evaluating the condition of the oil or of the wheel(s) of the mining truck as a function of the combination of variables measured and the history of the components recorded earlier; and
(g) Determining the type of defect that is occurring in real time, automatically, in accordance with the evaluation of step (f).

In the case where the system has the communication II embodiment incorporated, wherein a receiving antenna module (F) has been incorporated, the method also comprises: providing a receiving antenna module (F) that is located on the exterior of the mining truck, in order to wirelessly transmit the measurement data for the setting(s) from the wireless sensor module (A) to the server (G) in the communication II embodiment.

In the case where the system has the communication embodiment III incorporated, wherein a transmitter (H) has also been incorporated, the method also comprises: providing a processing box or transmitter (H) and wirelessly transmitting the measurement date from the setting(s) from the receiving antenna module (F) to the transmitter (H) and from the transmitter (H), wirelessly to the server (G).

Optionally, the data obtained by the wireless sensor module (A) can be analyzed in step (b) and be recorded through the server (G), via the analysis of the on line electrical signature of the measurement data and comparing said electrical signature with the database of electrical signatures associated with previously recognized defects.

Wherein step (a) of providing a wireless sensor module (A) comprises, mainly in its interior, an energy source (3), an electronic module (4) and an oil sensor (5) which must remain in constant contact with the oil inside the wheel (B).

The energy source (3) can be a rechargeable battery or not, or can be energy storing batteries coupled to sources of solar energy, or sources of energy generated by vibrations/movement, wherein a device transforms the vibrations/movements of the wheel into current and voltage, or sources of energy generated by differences in temperature, wherein a device transforms the energy generated by temperature differences into current and voltage. Wherein the temperature difference is measured by the Peletier thermo-electric effect, between the temperature of the oil that is in contact with the sensor nose and the outside air temperature in contact with a wall of the sensor.

Wherein, in step (a) of providing a wireless sensor module (A) the layout of the components in its interior can be chosen from: random layout or concentric modular layout.

Wherein, in the case of a concentric and modular layout, it is possible to take maximum advantage of the geometry of the wireless sensor module (A) and the modularity makes it possible to handle each one of the components inside the wireless sensor module (A) independently.

Wherein, in a preferred embodiment, step (a) of providing a wireless sensor module (A), which is preferably found in a modular and concentric layout, comprises the steps of:
(i) Laying out, in a concentric and modular manner, the following components: a coupling piece (1), a dome (2), at least one battery pack (3), an electronic module (4), an oil quality sensor (5) and a central axle (6);
(ii) Screwing the oil quality sensor (5) into the coupling piece (1);
(iii) Inserting the central axle (6) under pressure onto the oil sensor (5);
(iv) Inserting at least one battery pack (3) with its connectors facing the electronic module (4), with polarized positions around the central axle (6) on the coupling piece (1);
(v) Bolting the base of the coupling piece (1) into the electronic module (4) in the space left by the at least one battery pack (3), wherein the electronic module (4) is comprised of two components (D, E) interconnected to each other;
(vi) Connecting the connector of the at least one battery pack (3) to the supply module (D) of the electronic module (4), wherein the supply module (D) has an on/off switch (11);
(vii) Connecting the oil quality sensor (5) to the control module (E) of the electronic module (4), using a connector that is located in the inside of the control module (E); and
(viii) Hermetically sealing the wireless sensor module (A), screwing the dome (2) to the coupling piece (1).

Wherein the preferred method of the invention with the wireless sensor module (A), also comprises: turning on the wireless sensor module (A) through an access to the on/off switch (11); and hermetically sealing the access to the on/off switch (11) with a bolt-type piece, mounted with an o-ring by means of a silicone top that has a flap for assembling and disassembling, with the fingers, and which is inserted under pressure.

Wherein the measurement step (b) of one or more of the settings in the transmission system oil of the at least one wheel (B) of the mining truck consists of maintaining the nose of the oil quality sensor (5) in permanent contact with the oil inside the wheel (B) of the mining truck, wherein said permanent contact is achieved using a spoon-type mechanical device (7), maintaining the oil horizontal in order to prevent its dropping when the wheel (B) rotates.

In one of the preferred embodiments of the invention, there are perforations in the spoon-type mechanism (7), in order to enable a regeneration or circulation of the oil in the spoon-type mechanism.

The contamination settings measured by the oil quality sensor (5) may correspond to water, dust or another type of oil, such as, for example, brake oil.

Wherein the step of providing a receiving antenna module (F) comprises providing a housing (15) in which the interior has an electronic module (16), mounted by means of metallic spacers in order to give it the necessary height, wherein the electronic module (16) communicates with the wireless sensor module (A) and with the server (G), wirelessly, and communicates with the transmitter (H) by wire. An RF antenna (17) extends from the electronic module (16), which is mounted on a plastic capsule type piece (18) toward the exterior of the housing (15), preventing the signal from being blocked, wherein the assembly of the plastic capsule (18) is done by screwing on. Taking care to ensure that the location of the receiving antenna (F) enables open communication between the RF antenna (17) and the oil quality sensor (5) inside the truck wheel (B), positioning the housing (15) so that the RF antenna (17) is directed toward the oil quality sensor (5), either in front or on the side.

The invention claimed is:

1. A system for constantly monitoring a state of oil of wheels of machinery while in motion, comprising: a server to which a user has access and where databases with measurement parameters are stored; a wireless sensor module, connected to a rim of the wheel of a truck that obtains oil measurements from an oil quality sensor and wirelessly sends the oil measurements to the server; a sensor located inside the wireless sensor module and configured to obtain oil measurements within the wheel; and a spoon-like mechanical device configured to maintain the oil quality sensor in permanent contact with the oil in the wheel and rotates with the wireless sensor module and the wheel.

2. The system of claim 1, comprising: a receiving antenna module located on a side of the truck which wirelessly receives the oil measurements from the wireless sensor module and sends it wirelessly to the server; and a processing box and transmitter capable of receiving the oil measurements coming from the sensor which is in direct contact with the oil, processing it, storing it in a storage medium, backing it up and uploading it to the server, wherein the transmission of data from the sensor is done wirelessly to the receiving antenna module, which transmits the data by wire to the transmitter and from there, the data is wirelessly transmitted to the server.

3. The system of claim 2, wherein an electronic module wirelessly communicates the oil quality sensor with the receiving antenna module, and then to the server, or wherein the electronic module wirelessly communicates the oil quality sensor with the receiving antenna module, then to the transmitter, and finally to the server.

4. The system of claim 2, wherein the receiving antenna module comprises: a housing which is a water-resistant cabinet which is configured to protect an electronic module; the electronic module which is a circuit configured to intercommunicate the wireless sensor module directly with the server, capable of delivering and receiving data by RF with the wireless sensor module and of communicating wirelessly with the server; and an RF module which corresponds to a receiving antenna that enables communication with the wireless sensor module, wherein the housing is made of electro painted metallic material and has a hermetic design with an o-ring type perimeter seal, where closing the housing is done by means of chased screws; in the interior of the housing the electronic module is stored, mounted by means of metallic spacers; wherein the electronic module intercommunicates the receiving antenna module with the transmitter by wire and is capable of delivering and receiving data by RF with the wireless sensor module; and wherein from the electronic module extends the RF antenna, mounted in a plastic capsule-type piece toward the exterior of the housing, in order to prevent the metal from blocking the signal, wherein the assembly of this plastic capsule is done with screws, and is fully hermetic, to provide protection to both the RF antenna and the inside of the housing, wherein the modular connection of the RF antenna is by means of a plastic burlap clamp wherein said connector connects by wire to the transmitter.

5. The system of claim 2, wherein the transmitter comprises: a central processing unit (CPU) consisting of a controller with a processor, which is configured to receive the data from the oil quality sensor which is found inside the wheel of the truck, generating measurement archives, backing them up and uploading them to the server; an energy source, which is chosen from batteries that are rechargeable or not rechargeable, UPS, supply from the truck or solar energy; a device that enables communication between the transmitter and the server, and an antenna; a global positioning system which corresponds to a device capable of detecting a physical location of the truck and delivering it as data to the CPU; input ports for analog/digital signals; and a USB/RS-422 converter which corresponds to a device that is capable of delivering, by USB to the CPU, the data received by RS-422 from the receiving antenna modules of the wheels of the truck, wherein the transmitter has two converters, one per each receiving antenna module.

6. The system of claim 1, wherein the wireless sensor module comprises, in its interior, in energy source, an electronic module, and an oil sensor which must remain in constant contact with the oil inside the wheel; wherein the energy source is selected from: a rechargeable or non-rechargeable battery, or energy storing batteries coupled to sources of solar energy, or sources of energy generated by vibrations/movement, wherein a device transforms the vibrations/movements of the wheel into current and voltage, or sources of energy generated by differences in temperature, wherein a device transforms the energy resulting from the temperature differences between the oil in contact with a nose of the sensor and the temperature of the outside air in contact with a sensor wall, into current and voltage; and wherein the layout of components inside the wireless sensor module is selected from: a random layout or a concentric modular layout.

7. The system of claim 6, wherein when the layout of the components inside the wireless sensor module is a concentric layout comprising: a metallic coupling piece coupling the wireless sensor module to the rim of the wheel; a plastic dome configured to protect and hermetically seal the components inside it; a battery pack located inside a dome, configured to deliver energy for the autonomous operation of an electronic module and of the oil quality sensor; an electronic module located inside the dome, composed by two electronic capsules that execute all communication functions between the oil quality sensor and the server; the oil quality sensor, located inside the dome, that executes the measurements required by the user, within the wheel; and a central axle, located inside the dome, that is a mechanical piece that is configured to align components of the battery pack and electronic module in a concentric layout around the sensor, inside the coupling piece, protecting a sensor cable.

8. The system of claim 7, wherein the dome is designed and manufactured with UHMW (ultra-high molecular weight) plastic; wherein the coupling piece is made of stainless steel, wherein the assembly of the coupling piece to the wheel is done by means of a threaded piece that emulates a cap or magnetic plug of original oil, a piece replaced by the wireless sensor module; wherein the battery pack is positioned in a concentric layout in the coupling piece with a modular battery packaging, wherein the material used for the packaging is a heat-shrink polyvinyl chloride sleeve; and wherein the electronic module comprises two modules, a supply module and a control module, wherein the two modules have a defined position inside the coupling piece and are fixed to it with screws.

9. The system of claim 8, wherein the supply module is comprised of a profile of a corrugated or semi-circular section where a printed circuit plate, PCB, is stored, which is exposed in order to have access to a main connector for the batteries and an on/off switch; wherein the control module is a square section tube made of stainless steel which has, in its interior, two PCBs, interconnected face to face, wherein one of them has an RF communication module, an antenna that extends over the tube so as to not block the communication with the metal and, additionally, the tube has a lateral access for an input of energy coming from the supply module and for the input of cables coming from a connector of the oil quality sensor; and wherein access to the switch for turning the wireless sensor module on or off from an outside, without opening said module, is by means of a perforation through which the switch is turned on or off.

10. The system of claim 6, wherein the wireless sensor module has a random layout of its interior components and it is mounted to the wheel by a threaded piece.

11. A method for constantly monitoring a state of oil of wheels of machinery while in motion comprising: (a) providing a wireless sensor module to replace a magnetic cap in at least one of the wheels of a truck with said module; (b) measuring, through the wireless sensor module, one or more parameters in a transmission system oil of the at least one wheel of the truck, selected from: amount of particulate matter, temperature, contamination, permittivity or viscosity, through an oil quality sensor that is located inside the wireless sensor module; (c) providing a server where databases with the measurement parameters are stored; (d) transmitting measurement data of the parameters wirelessly to the server from the wireless sensor module; (e) processing the measurement data and comparing it with data previously recorded; (f) evaluating a condition of the oil or of the wheel of the truck as a function of a combination of measured variables and history of components previously recorded; and (g) determining a type of defect that is occurring in real time, automatically, in accordance with the evaluation of step (f); wherein measuring, through the wireless sensor module, one or more parameters in the transmission system oil of the at least one wheel of the truck comprises maintaining a nose of the oil quality sensor in permanent contact with the oil inside the wheel of the truck, wherein said permanent contact is achieved using a spoon-type mechanical device, maintaining the oil horizontal in order to prevent its dropping when the wheel rotates.

12. The method of claim 11, further comprising providing a receiving antenna module located on an exterior of the truck, in order to wirelessly transmit the measurement data for the parameter from the wireless sensor module to the server; and providing a processing box or transmitter and transmitting the measurement data of the parameter(s) by wire from the receiving antenna module to the transmitter and from the transmitter wirelessly to the server.

13. The method of claim 12, wherein providing the receiving antenna module comprises providing a housing in the interior of which is an electronic module mounted by means of metallic spacers, wherein the electronic module communicates with the wireless sensor module and with the server, wirelessly, wherein an RF antenna extends from the electronic module, which is mounted on a plastic capsule toward an exterior of the housing, preventing a signal from being blocked, wherein assembly of the plastic capsule is done by means of screws; wherein the electronic module communicates with the transmitter by wire; and wherein a location of the receiving antenna enables open communication between the RF antenna and the oil quality sensor inside the truck wheel, positioning the housing so that the RF antenna is directed toward the oil quality sensor, either in front or on the side.

14. The method of claim 11, wherein the wireless sensor module comprises, in its interior, an energy source, an electronic module and an oil sensor which must remain in constant contact with the oil inside the wheel; wherein the energy source is selected from: a rechargeable or non-rechargeable battery, or energy storing batteries coupled to sources of solar energy, or sources of energy generated by vibrations/movement, wherein a device transforms the vibrations/movements of the wheel into current and voltage, or sources of energy generated by differences in temperature, wherein a device transforms the energy resulting from the temperature differences between the oil in contact with a nose of the sensor and the temperature of the outside air in contact with a wall of the sensor, into current and voltage; and wherein providing the wireless sensor module comprises selecting a layout of components inside it from: random layout or concentric modular layout.

15. The method of claim 14, wherein when the layout of the components inside the wireless sensor module is a concentric layout comprising: laying out, in a concentric and modular manner, the following components: a coupling piece, a dome, at least one battery pack, the electronic module, an oil quality sensor, and a central axle; screwing the oil quality sensor into the coupling piece; pressure-fitting the central axle onto the oil quality sensor; inserting at least one battery pack with its connectors facing the electronic module, with polarized positions around the central axle on the coupling piece; bolting the base of the coupling piece into the electronic module in the space left by the at least one battery pack, wherein the electronic module is comprised of two components interconnected to each other; connecting the connector of the at least one battery pack to a supply module of the electronic module, wherein the supply module has an on/off switch; connecting the oil quality sensor to the control module of the electronic module, using a connector that is located in an inside of the control module; and hermetically sealing the wireless sensor module, screwing the dome to the coupling piece; wherein it further comprises the steps of turning on the wireless sensor module through an access to the on/off switch hermetically sealing the access to the on/off switch with a bolt-type piece, mounted with an o-ring by means of a silicone top that has a flap for assembling and disassembling and which is pressure-fitted.

16. The method of claim 11, wherein there are perforations in the spoon-type mechanism, in order to enable a regeneration or circulation of the oil in the spoon-type mechanism.

17. The method of claim 11, wherein the contamination parameters measured by the oil quality sensor correspond to water, dust or another type of oil.

* * * * *